United States Patent [19]
Lucey et al.

[11] Patent Number: 5,797,836
[45] Date of Patent: Aug. 25, 1998

[54] ENDOSCOPE WITH RELATIVE ROTATION AND AXIAL MOTION BETWEEN AN OPTICAL ELEMENT AND AN IMAGING DEVICE

[75] Inventors: Paul V. Lucey, Sandown; Robert J. Scarchilli, Nashua, both of N.H.

[73] Assignee: Smith & Nephew, Inc., Memphis, Tenn.

[21] Appl. No.: 475,898

[22] Filed: Jun. 7, 1995

[51] Int. Cl.⁶ .................................................. A61B 1/05
[52] U.S. Cl. ........................... 600/109; 600/167; 600/173
[58] Field of Search ........................... 600/173, 174, 600/171, 167, 137, 109, 117, 103, 112, 921; 348/65, 71, 73, 75, 66

[56] References Cited

U.S. PATENT DOCUMENTS

| | | |
|---|---|---|
| Re. 31,289 | 6/1983 | Moore et al. . |
| Re. 31,290 | 6/1983 | Moore et al. . |
| 4,253,447 | 3/1981 | Moore et al. . |
| 4,261,344 | 4/1981 | Moore et al. . |
| 4,273,109 | 6/1981 | Enderby . |
| 4,294,511 | 10/1981 | Yamashita et al. . |
| 4,491,865 | 1/1985 | Danna et al. ............................ 358/98 |
| 4,534,339 | 8/1985 | Collins et al. . |
| 4,639,772 | 1/1987 | Sluyter et al. ........................... 348/73 |
| 4,736,733 | 4/1988 | Adair . |
| 4,854,302 | 8/1989 | Allred, III . |
| 4,858,001 | 8/1989 | Milbank et al. ......................... 600/133 |
| 4,998,182 | 3/1991 | Krauter et al. . |
| 5,051,824 | 9/1991 | Nishigaki ................................ 600/109 |
| 5,191,879 | 3/1993 | Krauter ................................... 600/167 |
| 5,222,477 | 6/1993 | Lia . |
| 5,253,638 | 10/1993 | Tamburrino et al. ................... 600/170 |
| 5,331,950 | 7/1994 | Wood, Sr. . |
| 5,379,756 | 1/1995 | Pileski et al. . |
| 5,528,432 | 6/1996 | Donahou ............................... 348/66 X |

FOREIGN PATENT DOCUMENTS

| | | | |
|---|---|---|---|
| 592194 | 4/1994 | European Pat. Off. ............... 600/167 |
| 38 40 389 A1 | 11/1988 | Germany . |
| 659199 | 3/1994 | Japan ..................................... 385/117 |
| 1391611 | 4/1988 | U.S.S.R. ................................. 600/137 |
| 2 030 313 | 6/1978 | United Kingdom . |

*Primary Examiner*—John P. Leubecker
*Attorney, Agent, or Firm*—Fish & Richardson P.C.

[57] ABSTRACT

An apparatus for viewing a region comprises a hollow member elongated between a proximal end and a distal end configured to be inserted into the region, an optical element disposed in the distal end, and an image detector disposed adjacent to the optical element. The optical element and the image detector are arranged for relative rotation. The apparatus is particularly well-suited for use in an endoscope, and in particular with an endoscope having an off-axis field of view.

21 Claims, 3 Drawing Sheets

ENDOSCOPE WITH RELATIVE ROTATION AND AXIAL MOTION BETWEEN AN OPTICAL ELEMENT AND AN IMAGING DEVICE

BACKGROUND

This invention relates to imaging devices, and in particular to endoscopes.

Endoscopes are widely used to inspect regions of the body (e.g., joint spaces) through a small puncture wound during surgery (such as arthroscopic surgery). Typically, the endoscope includes an elongated insertion tube equipped with a set of optical fibers which extend continuously from a proximal handle, through the insertion tube to the distal viewing tip of the endoscope. A cable that rigidly attaches to the handle (e.g., at a post on the side of the handle) carries light from an external light source to the proximal end of the optical fibers, and the viewing end, where the light is emitted to illuminate the region under inspection.

Received light representing an optical image of the joint space is collected by an optical element (such as one or more lenses of a lens assembly) mounted in the distal viewing tip and is passed to, e.g., a solid-state image detector (such as a charge-coupled-device, or CCD). The CCD converts the received optical image to electrical signals that are processed for viewing on a display.

Some endoscopes have a direction of view (i.e., the direction along which the endoscope emits and receives light) along the longitudinal axis of the insertion tube. The distal viewing ends of other endoscopes are constructed to provide an off-axis direction of view (e.g., at 30° or at 70°).

SUMMARY OF THE INVENTION

This invention features an imaging device in which the image detector and the optical element are arranged for relative rotation. The invention is particularly, but by no means exclusively, useful in an endoscope that has an off-axis direction of view, because it allows the user to control the orientation of the displayed image when the endoscope is rotated to change the field of view. As a result, the user can maintain the displayed image in any orientation that he or she selects, regardless of the rotational position of the endoscope.

In one aspect of the invention, the optical element and the image detector are disposed adjacent to each other and arranged for relative rotation in the distal end of an elongated, hollow member.

Preferred embodiments include the following features.

An actuator is arranged to provide the relative rotation between the optical element and the image detector. preferably, the actuator is rotatably disposed with respect to the proximal end of the hollow member and is coupled to the image detector so that rotation of the actuator causes the image detector to rotate with respect to the optical element (which is stationary with respect to the hollow member).

The image detector (e.g., a solid state pickup device) is supported at the distal end of an elongated inner member disposed within the hollow member. The actuator engages the proximal end of the inner member. This engagement is configured to permit the inner member to be moved axially with respect to the hollow member to change the spacing between the image detector and the optical element. This feature allows the image to be focussed on the image detector without interference from the linkage to the actuator.

In one embodiment, the engagement between the actuator and the proximal end of the inner member is provided by a key on the actuator that is disposed in a slot in the proximal end of the inner member. The slot has a longitudinal length sufficient to allow the inner member to move axially with respect to the hollow member. A second actuator is linked to the proximal end of the inner member for moving the inner member axially (e.g., during the focussing operation).

The optical element is configured to provide an off-axis direction of view—that is, a direction of view that is at a nonzero angle with respect to the axis of the hollow member. preferably, the optical element includes at least one lens.

Another aspect of the invention features a method of viewing a region of the body using an endoscope that implements structural features of the invention. The endoscope is inserted into the body and placed in a first rotational position so that an image of the body region detected by the image detector is displayed in a first orientation on a display device; then, the endoscope is rotated to a second, different rotational position and the actuator is manipulated so that the image of the body region is displayed in the first orientation.

Preferred embodiments include the following features.

The overall result —displaying the image in the first rotational position despite rotating the endoscope—can be achieved in multiple ways. For example, the endoscope may first be rotated to the second rotational position so that the image is displayed in a second, different orientation on the display device; the actuator is then rotated to cause the displayed image to return to the first orientation. Alternatively, the endoscope is rotated to the second rotational position while holding the actuator stationary so that the image remains in the first displayed orientation as the endoscope is rotated.

The invention allows the user to rotate the endoscope at will (e.g., to change the direction of view as necessary during surgery) without necessarily rotating the displayed image. The orientation of the displayed image can be maintained in any selected orientation independently of the rotational position of the endoscope. As a result, even when the endoscope is rotated by, e.g., 180 degrees, the user need not view the image "upside down."

Moreover, rotating the image detector with respect to the optical element enables an external fiber optic cable, which receives light from an external light source, to be connected in-line at the proximal end of the handle (rather than at a side-facing light post on the handle). Connecting the fiber optic cable to the handle in this way reduces the tendency of the fiber optic cable to become twisted or wrapped around the handle when the endoscope is rotated. This enhances the maneuverability of the endoscope, and substantially reduces the risk of damaging the fiber optic cable (and its associated connectors).

Other features and advantages of the invention will become apparent from the following detailed description, and from the claims.

BRIEF DESCRIPTION OF THE DRAWINGS

FIG. 4 is a cross-section of the endoscope handle, taken along line 4—4 of FIG. 3.

DESCRIPTION OF A PREFERRED EMBODIMENT

Figure 1:
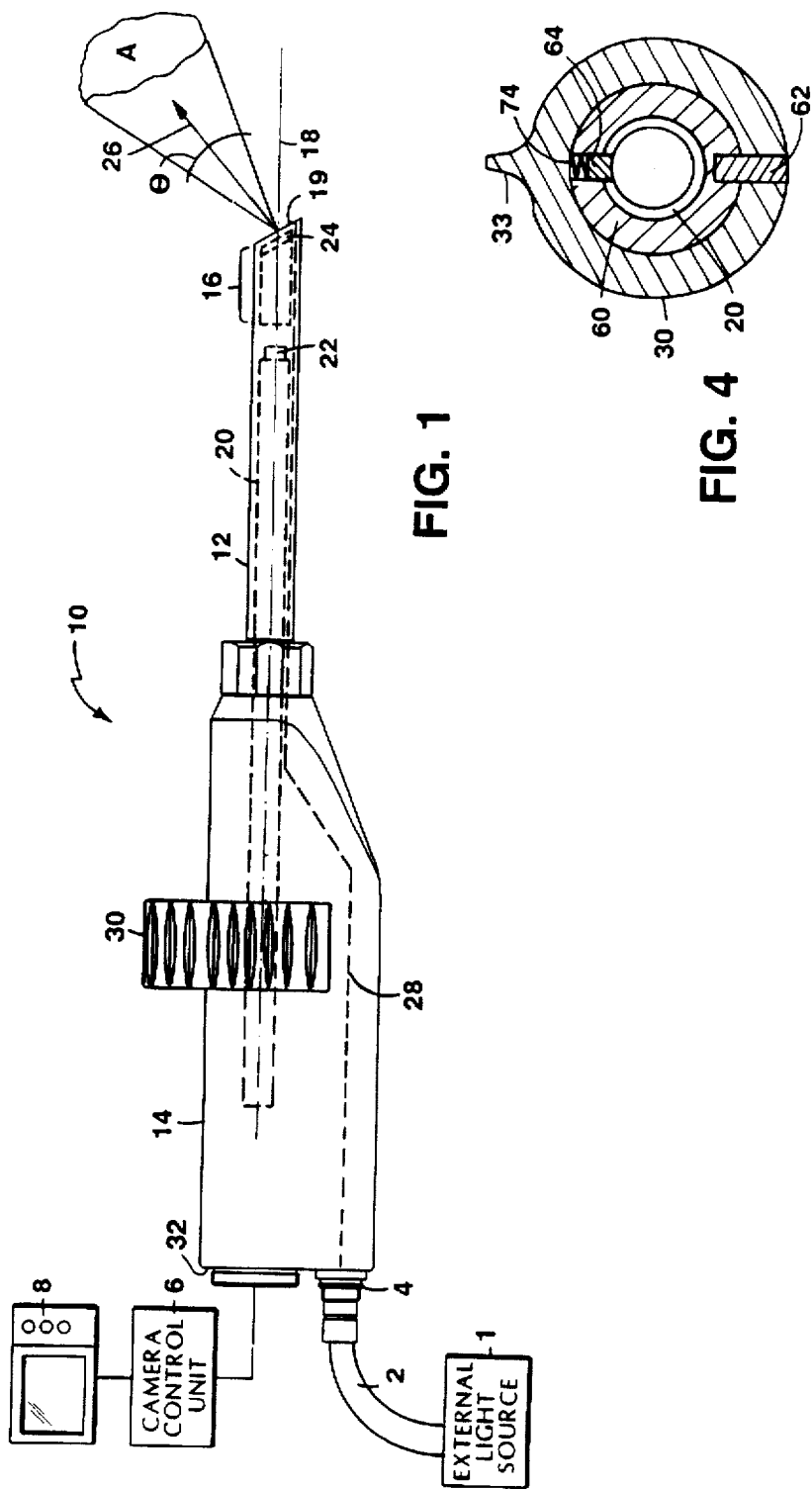
FIG. 1 is a diagrammatic view of an endoscope.

Referring to FIG. 1, endoscope 10, suitable for viewing inside of a remote area, such as, for example, viewing into a body cavity, joint space, or passageway during arthroscopic surgery, includes elongated insertion tube 12 attached to handle 14. Lens assembly 16 (shown schematically) is mounted within the distal end of insertion tube 12. CCD tube 20 supports a charge-coupled device (CCD) or other suitable image detector 22 proximally adjacent to lens assembly 16. CCD tube 20 and CCD are rotatably mounted with respect to lens assembly 16, about longitudinal axis 18, within insertion tube 12 and handle 14. Actuator 30 is linked to the proximal end of CCD tube 20 and is rotatably mounted to handle 14. As described in more detail below, actuator 30 is manipulated by a user to produce relative rotation between CCD tube 20 (and thus CCD 22) and insertion tube 12 about longitudinal axis 18.

Endoscope 10 has a direction of view (shown by vector 26 in FIG. 1) that is off-axis, i.e., arranged at a nonzero angle to longitudinal axis 18. The direction of view is determined by the orientation of window lens 24 of lens assembly 16 (i.e., the angle formed between longitudinal axis 18 and vector 26, vector 26 being perpendicular to window lens 24 at distal viewing tip 19) and is typically 30°, 45°, or 70°. The field of view, angle Θ, is an angle within which the endoscope receives light from external objects, i.e., the angle over which the endoscope "sees," and is equidistant on either side of vector 26.

Endoscope 10, as shown, views area A. To illuminate area A, endoscope 10 includes a set 28 of optical fibers 29 that extend through handle 14 and insertion tube 12 to distal viewing tip 19. Light from external light source 1 is transmitted through light cable 2 to a light coupler 4 at the back of handle 14, which is in turn connected to one end of optical fiber set 28. The arrangement of optical fibers 29 at distal viewing tip 19 is described briefly below and in more detail in U.S. patent application Ser. No. 08/475,900 "Rotatable Fiber Optic Joint," filed concurrently with this patent application, assigned to the present assignee, and incorporated herein by reference.

In use, light from external light source 1 is coupled through cable 2 and optical fiber set 28, and exits distal viewing tip 19 to illuminate area A. Light from objects within area A is collected by lens assembly 16 and passed to CCD 22, which converts the light into electrical signals representing the objects. The electrical signals are transmitted (by circuitry not shown) to a camera control unit 6 for processing in the usual manner. The resultant image is displayed on display screen 8.

The user rotates handle 14 and insertion tube 12 together about longitudinal axis 18 to change the orientation of the field of view and observe areas adjacent to area A. All other things being equal, rotating handle 14 causes the image projected onto display screen 8 to be rotated, as well, because CCD tube 20 and CCD 22 are rotated with insertion tube 12. But with the invention, the user can readjust the orientation of the image on display screen 8 and reorient the displayed image in its original orientation simply by rotating actuator 30. As a result, the user can continue to view the image in the original orientation, despite having rotated endoscope 10.

Figure 2:
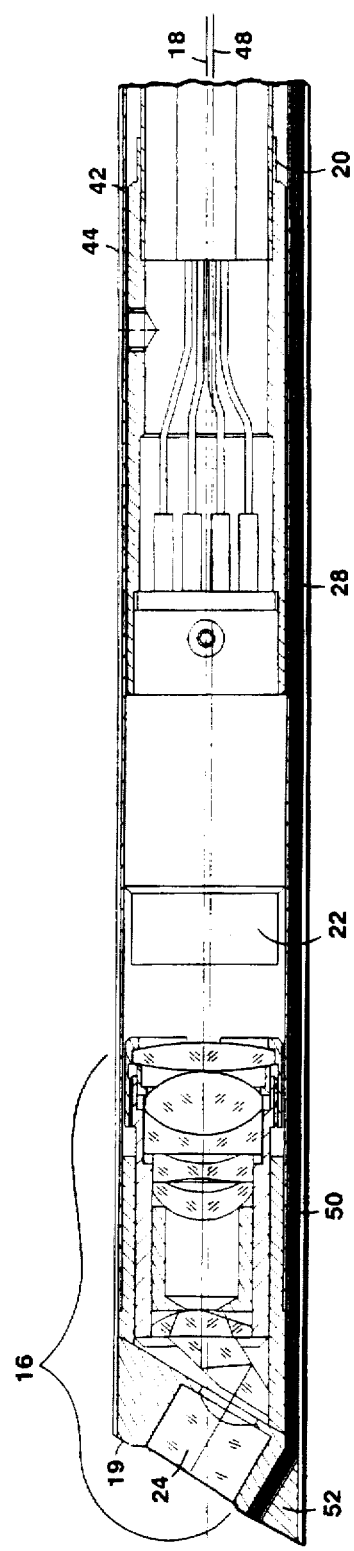
FIG. 2 is a cross-sectional side view of the insertion tube of the endoscope of FIG. 1.

Referring as well to FIG. 2, insertion tube 12 includes inner tube 42, which houses CCD tube 20, and outer tube 44. Inner tube 42 and outer tube 44 extend along different, parallel axes—longitudinal axis 18 and longitudinal axis 48, respectively. The offset between longitudinal axis 18 and longitudinal axis 48, which is preferably about 0.013 inches, creates a channel 50 between tubes 42, 44. Channel 50 houses optical fiber set 28 in insertion tube 12.

At distal viewing tip 19, lens assembly 16 is aligned along longitudinal axis 18. Window lens 24 of lens assembly 16 is angled with respect to the longitudinal axis 18 to determine the direction of view of endoscope 10, and could be recessed from the distal end of outer tube 44 to protect the exposed exterior surface of window lens 24. Wedge 52, at distal viewing tip 19, deflects optical fibers 28 such that light is directed along the direction of view in accordance with the orientation of window lens 24, e.g., at 30° with respect to axis 18. Individual optical fibers 29 of optical fiber set 28 are arranged in a crescent shape within wedge 52, corresponding to the shape of channel 50, to evenly disperse the light across the width of insertion tube 12. Lens assembly 16, wedge 52, optical fibers 28, and outer tube 44 are all bonded together by, for example, an epoxy. Lens assembly 16 is also attached to inner tube 42 by, for example, an epoxy. The construction of distal viewing tip 19 is also described in the above-identified patent application.

CCD 22 is positioned proximally of lens assembly 16 and is aligned along longitudinal axis 18. CCD tube 20 is rotatably mounted within inner tube 42 of insertion member 12 and handle 16 in a manner described in detail below. Additionally, CCD tube 20 is axially movable along longitudinal axis 18 within inner tube 42 and handle 14 to adjust the focus of the image detected by CCD 22. CCD 22, including its associated electrical and optical systems, are of the type described in detail in copending U.S. patent application Ser. No. 07/958,688, filed Oct. 9, 1992, incorporated herein by reference.

In particular, as described in the '668 application, upon manipulation of a focusing mechanism by a user, CCD tube 20 and CCD 22 are moved axially along longitudinal axis 18 with respect to lens assembly 16. This motion changes the spacing between lens assembly 16 and CCD 22, thereby adjusting the focus of the image. The focussing mechanism of endoscope 10 differs in some respects from that described in the '668 application, as described below.

Figure 3:
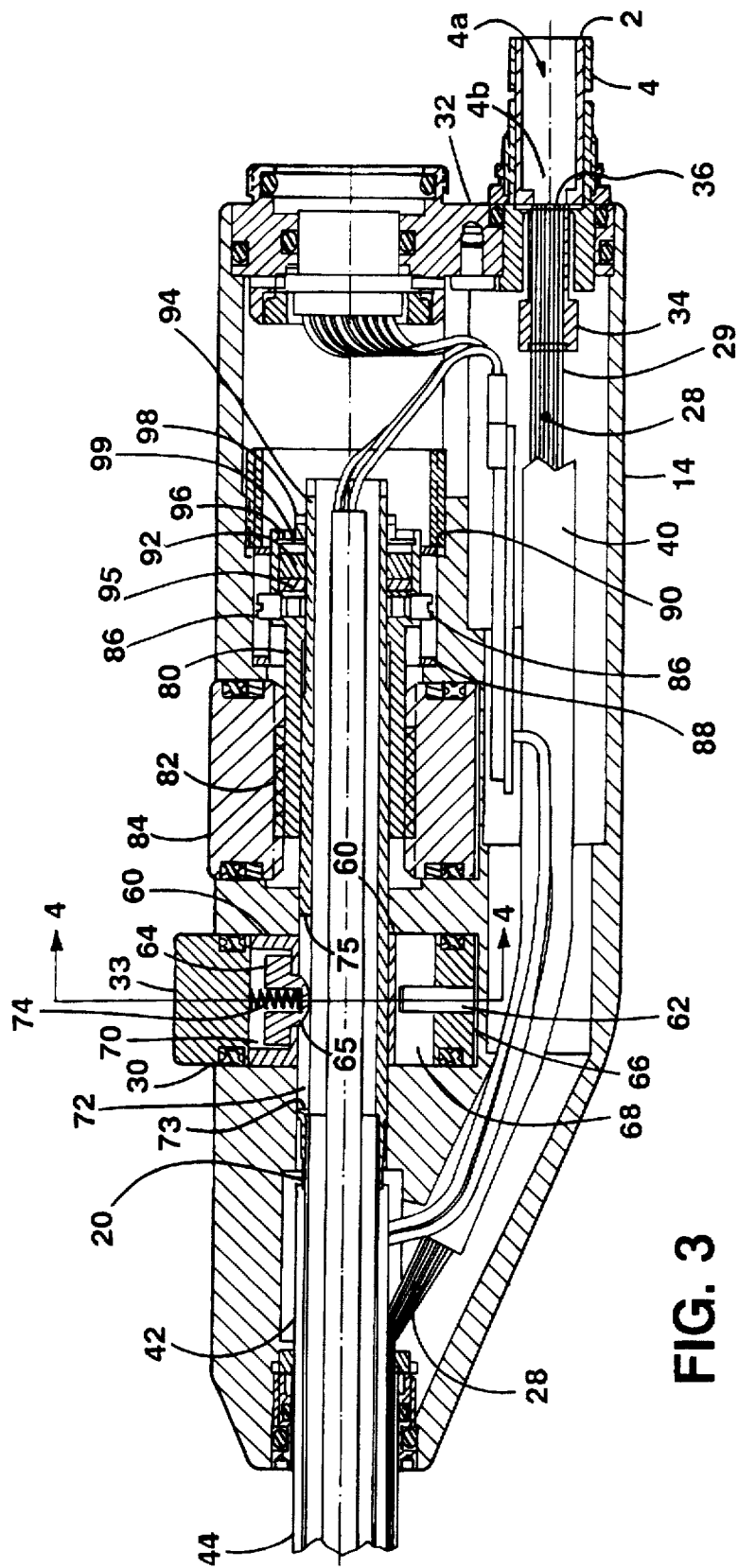
FIG. 3 is an enlarged cross-sectional side view of the handle of the endoscope of FIG. 1.

Referring to FIGS. 3 and 4, the proximal end of CCD tube 20 is engaged by actuator 30. More specifically, actuator 30 is coupled by pin 62 to bushing 60, which in turn is linked to CCD tube 20 by key 64. In particular, pin 62 is inserted through bore 66 in actuator 30, into a first longitudinal slot 68 in bushing 60. Key 64 is disposed within a second longitudinal slot 70 in bushing 60, so that a rounded portion 65 of key 64 extends into a slot 72 in CCD tube 20. Key 64 is biased into slot 72 by spring 74, which urges key 64 away from an interior surface of the body of actuator 30. Rotation of actuator 30 about longitudinal axis 18 is translated through pin 62, bushing 60, and the engagement of key 64 in slot 72 to cause CCD tube 20 (and thus CCD 22) to rotate about axis 18. Notably, during the assembly or disassembly of CCD tube 20 from endoscope 10, rounded portion 65 of key 64 functions as a cam against the exterior surface of CCD tube 20 (including slot 72 and slot edges 73, 75). For example, as CCD tube 20 is axially removed from endoscope 10, rounded portion 65 engages slot edge 75 to push key 64 against spring 74 such that key 64 is removed from slot 72.

The body of actuator 30 includes a raised ridge 33 aligned with the vertical dimension of the imaging surface of CCD 22. Ridge 33 gives the user a frame of reference to determine the rotational position of CCD 22 with respect to handle 14 (and thus insertion tube 12). Ridge 33 also provides the user with a convenient way of holding CCD 22 rotationally stationary, if desired, when handle 14 and insertion tube 12 are rotated.

FIG. 3 shows the mechanism used to move CCD 22 axially with respect to lens assembly 16 for adjusting focus.

The proximal end of focus sleeve 80 includes threads 82 that engage threads on focus knob 84. When focus knob 84 is rotated, focus sleeve 80 is prevented from rotating by the engagement of pins 86 within elongated slots in a stationary alignment ring 88. Alignment ring 88 is retained in handle by retaining ring 90. Thus, rotational motion of focus knob 84 is translated into axial movement of focus sleeve 80, which is attached to CCD tube 20 (by lock nut 98 and washer 99 being tightened against focus adjustment nut 92), thereby causing CCD tube 20 to also move axially. Slot 72 in CCD tube 20 and the slots in alignment ring 88 are of sufficient length to permit the axial movement of CCD tube 20 for focusing.

The initial focus position of endoscope 10 is preset during manufacture as follows. The proximal end of CCD tube 20 includes threads 94 which are engaged by the threads of a focus adjustment nut 92. When focus adjustment nut 92 is rotated, wave spring 95 pushes focus adjustment nut 92 proximally into retainer ring 96 to translate rotation of focus adjustment nut 92 to axial movement of CCD tube 20. When infinity (i.e., the initial "in focus" position) is located, focus adjustment nut 92 is locked into position by tightening lock nut 98 and washer 99 against focus adjustment nut 92. This arrangement of focus adjustment nut 92, lock nut 98 and washer 99 also secures the proximal end of CCD tube 20 within handle 14. The distal end of CCD tube 20 is mounted in inner tube 42, and aligned about longitudinal axis 18, by the close tolerance between CCD tube 20 and inner tube 42.

FIG. 3 also shows the connection between external fiber optic cable (FIG. 1) and optical fiber set 28 at the proximal end 32 of handle 14. The individual fibers 29 of set 28 (each of which is approximately 2.0 mils in diameter) are epoxied into threaded bushing 34, and the proximal ends 36 of each optical fiber 29 are uniformly polished for efficiently receiving light from light coupler 4. A sheath 40 covers and bundles individual optical fibers 29 through a substantial portion of handle 14.

Light coupler 4 is designed to change the numerical aperture of light cable 2, which has a relatively low value (e.g., 0.54) for efficient light transfer, to a higher value (e.g., 0.81), which is desirable for adequately illuminating area A (FIG. 1). This is done by providing light coupler 4 with different inside diameters 4a, 4b at its ends. That is, diameter 4a is relatively large (5 ¼ mm) where cable enters coupler 4, and is reduced substantially (to a diameter, 4b, of 3 ½ mm) at the junction between cable 2 and optical fiber set 28. The ratio between diameters 4a and 4b multiplied by the numerical aperture of cable 2 (0.54) provides the desired numerical aperture (0.81) of optical fiber set 28.

In use, insertion tube 12 of endoscope 10 is inserted into a body cavity, joint space, or passageway during surgery. Distal viewing tip 19 is oriented by a user such that the desired area within the body cavity is within the field of view of endoscope 10 and displayed on display screen 8. To view a different part of the body cavity, the user rotates handle 14, e.g., clockwise, which causes insertion tube 12, CCD tube 20, and CCD 22, to rotate in the same direction about longitudinal axis 18. Thus, not only is the direction of view changed, so too is the orientation of the image on display screen 8. To reorient the image on in its initial orientation on display screen 8, the user rotates actuator 30 in a direction opposite from the rotation of handle 14 (e.g., counterclockwise) until the image is properly oriented on display screen 8.

The user can avoid this two step procedure and maintain the orientation of the displayed image fixed by holding actuator 30 stationary (ridge 33 provides a convenient grasping point) while rotating handle 14. This causes CCD tube 20 (and hence CCD 22) to remain stationary while insertion tube 12 rotates about CCD tube 20.

Other embodiments are within the scope of the following claims.

For example, inner tube 42 and outer tube 44 may be coaxial so that the channel created for optical fibers 29 is an annular ring formed between the inner and outer tubes. Likewise, other arrangements of individual optical fibers 29 at distal viewing tip 19 can be used. For example, optical fibers 29 can be arranged in an annular ring about the perimeter of window lens 24.

The endoscope can include any of the features of the above identified patent applications. For example, as described in the "Rotatable Fiber Optic Joint" application, the endoscope may allow the insertion tube to be rotated with respect to the handle, and include a rotatable joint between discrete sets of optical fibers in the handle and in the insertion tube, respectively.

What is claimed is:

1. An apparatus for viewing a region, comprising:
    a hollow member elongated between a proximal end and a distal end configured to be inserted into the region,
    an elongated inner member disposed within said hollow member,
    an optical assembly comprising
        an optical element disposed in said distal end of said hollow member, and
        an image detector supported at a distal end of said inner member adjacent said optical element in said distal end, and
        an actuating mechanism coupled to said optical assembly and arranged to separately produce: (1) relative rotation between said optical element and said image detector, and (2) relative axial motion between said optical element and said image detector to change a spacing therebetween,
    said actuating mechanism including an actuator arranged to provide said relative rotation between said optical element and said image detector, said actuator being rotatable disposed with respect to said proximal end of said hollow member and engaging a proximal end of said inner member so that rotation of said actuator causes said image detector to rotate with respect to said optical element, the engagement between said actuator and said proximal end of said inner member being configured to permit said inner member to be moved axially with respect to said hollow member to change said spacing between said image detector and said optical element.

2. The apparatus of claim 1 wherein said optical element is stationary with respect to said hollow member.

3. The apparatus of claim 1 wherein said image detector is a solid-state image pickup device.

4. The apparatus of claim 1 wherein said hollow member is elongated along a longitudinal axis, said optical element being configured to provide a direction of view at a nonzero angle with respect to said axis.

5. The apparatus of claim 1 wherein said optical element includes at least one lens.

6. An apparatus for viewing a region, comprising:
    a hollow member elongated between a proximal end and a distal end configured to be inserted into the region,
    an optical element disposed in said distal end of said hollow member,

7 an elongated inner member disposed within said hollow member, an image detector supported at a distal end of said inner member adjacent said optical element, said optical element and said image detector being arranged for relative rotation, and an actuator engaging a proximal end of said inner member for providing said relative rotation between said optical element and said image detector, the actuator rotatable disposed with respect to said proximal end of said hollow member and coupled to said image detector so that rotation of said actuator causes said image detector to rotate with respect to said optical element, the engagement between said actuator and said proximal end of said inner member being configured to permit said inner member to be moved axially with respect to said hollow member to change a spacing between said image detector and said optical element, said engagement being provided by a key on said actuator disposed in a slot in said proximal end of said inner member, said slot having a longitudinal length sufficient to allow said inner member to move axially with respect to said hollow member.

7. The apparatus of claim 6 further comprising a second actuator linked to said proximal end of said inner member for moving said inner member axially with respect to said hollow member.

8. The apparatus of claim 6 wherein said image detector is a solid-state image pickup device.

9. The apparatus of claim 6 wherein said hollow member is elongated along a longitudinal axis, said optical element being configured to provide a direction of view at a nonzero angle with respect to said axis.

10. The apparatus of claim 6 wherein said optical element includes at least one lens.

11. The apparatus of claim 6 further comprising an optical fiber extending through said hollow member for delivering light to said distal end of said hollow member.

12. The apparatus of claim 6 wherein said hollow member extends along a first longitudinal axis and said inner member extends along a second different longitudinal axis, said first and second longitudinal axes being parallel and being offset sufficiently to provide a channel within said hollow member to allow light to be carried to said distal end of said hollow member.

13. An apparatus for viewing a region, comprising:

a hollow member elongated between a proximal end and a distal end configured to be inserted into the region, an elongated inner member disposed within said hollow member, an optical element disposed in said distal end of said hollow member, an image detector supported at a distal end of said inner member and disposed adjacent said optical element, and an actuating mechanism including:

a first actuator rotatable disposed with respect to said proximal end of said hollow member and engaging a proximal end of said inner member so that rotation of said first actuator causes said image detector to rotate with respect to said optical element, wherein the engagement between said first actuator and said proximal end of said inner member is configured to permit said inner member to be moved axially with respect to said hollow member; and a second actuator linked to said proximal end of said inner member for moving said inner member axially

8 with respect to said hollow member, thereby to chance a spacing between said image detector and said optical element.

14. An endoscope comprising:

a handle, an insertion member elongated between a proximal end attached to said handle and a distal end, an optical element disposed in said distal end of said insertion member, an image detector, an inner member disposed within said insertion member for relative rotation therewith, said inner member having a distal end supporting said image detector adjacent to said optical element, and an actuating mechanism coupled to said inner member for separately producing: (1) relative rotation between said optical element and said image detector, and (2) relative axial motion between said optical element and said image detector to change a spacing therebetween, said actuating mechanism including an actuator arranged to provide said relative rotation between said optical element and said image detector, said actuator being rotatable disposed with respect to said proximal end of said insertion member and engaging a proximal end of said inner member so that rotation of said actuator causes said image detector to rotate with respect to said optical element, the engagement between said actuator and said proximal end of said inner member being configured to permit said inner member to be moved axially with respect to said hollow member to change said spacing between said image detector and said optical element.

15. The endoscope of claim 14 wherein said insertion member is elongated along a longitudinal axis, said optical element being configured to provide a direction of view at a nonzero angle with respect to said axis.

16. A method of viewing a region of the body comprising the steps of inserting into the body an endoscope having a hollow member elongated between a proximal end and a distal end configured to be inserted into the region, an elongated inner member disposed within said hollow member, an optical element disposed in said distal end of said hollow member, an image detector supported at a distal end of said inner member adjacent said optical element in said distal end, and an actuating mechanism arranged to produce relative rotation between said optical element and said image detector and relative axial motion between said optical element and said image detector to change a spacing therebetween, said actuating mechanism including an actuator arranged to provide said relative rotation between said optical element and said image detector, said actuator being rotatably disposed with respect to said proximal end of said hollow member and engaging a proximal end of said inner member so that rotation of said actuator causes said image detector to rotate with respect to said optical element, the engagement between said actuator and said proximal end of said inner member being configured to permit said inner member to be moved axially with respect to said hollow member to change said spacing between said image detector and said optical element, placing said endoscope in a first rotational position so that an image of said region detected by said image detector is displayed in a first orientation on a display device, rotating said endoscope to a second, different rotational position and manipulating said actuator to cause said image of said region to be displayed in said first orientation on the display device, and further manipulating said actuator to change the spacing between said optical element and said image detector thereby to focus said image.

17. The method of claim 16 wherein said step of rotating and manipulating includes first rotating said endoscope to said second rotational position so that said image is displayed in a second, different orientation on the display device, and then manipulating said actuating mechanism to cause said displayed image to return to said first orientation.

18. The method of claim 16 wherein said step of rotating and manipulating includes rotating said endoscope to said second rotational position while holding said actuating mechanism stationary so that said image remains in said first orientation on the display device as said endoscope is rotated.

19. The method of claim 16 wherein the step of further manipulating said actuating mechanism is performed prior to said rotating and manipulating step.

20. The method of claim 16 wherein the step of further manipulating said actuating mechanism is performed after said rotating and manipulating step.

21. A method of viewing a region of the body, the method comprising the steps of inserting into the body an apparatus for viewing the region, the apparatus comprising
- a hollow member elongated between a proximal end and a distal end configured to be inserted into the region,
- an optical element disposed in said distal end of said hollow member,
- an elongated inner member disposed within said hollow member,
- an image detector supported at a distal end of said inner member adjacent said optical element, said optical element and said image detector being arranged for relative rotation, and
- an actuator engaging a proximal end of said inner member for providing said relative rotation between said optical element and said image detector, the actuator rotatably disposed with respect to said proximal end of said hollow member and coupled to said image detector so that rotation of said actuator causes said image detector to rotate with respect to said optical element, the engagement between said actuator and said proximal end of said inner member being configured to permit said inner member to be moved axially with respect to said hollow member to change a spacing between said image detector and said optical element, said engagement being provided by a key on said actuator disposed in a slot in said proximal end of said inner member, said slot having a longitudinal length sufficient to allow said inner member to move axially with respect to said hollow member, placing said apparatus in a first rotational position to cause an image of said region detected by said image detector to be displayed in a first orientation on a display device, rotating said apparatus to a second, different rotational position and manipulating said actuator to cause said image of said region to be displayed in said first orientation on the display device, and moving said inner member axially with respect to said hollow member to change the spacing between said optical element and said image detector and focus said image.

\* \* \* \* \*

UNITED STATES PATENT AND TRADEMARK OFFICE
CERTIFICATE OF CORRECTION

PATENT NO. : 5,797,836

DATED : August 25, 1998

INVENTOR(S) : Paul V. Lucey et al.

It is certified that error appears in the above-identified patent and that said Letters Patent is hereby corrected as shown below:

Col. 3, line 34, after "08/475,900" insert --entitled--.

Col. 6, claim 1, line 43, replace "rotatable" with --rotatably--.

Col. 7, claim 6, line 9, replace "rotatable" with --rotatably--.

Col. 7, claim 13, line 57, replace "rotatable" with --rotatably--.

Col. 8, claim 13, line 2, replace "chance" with --change--.

Col. 8, claim 14, line 23, replace "rotatable" with --rotatably--.

Signed and Sealed this

Twelfth Day of January, 1999

Attest:

*Attesting Officer*  *Acting Commissioner of Patents and Trademarks*